United States Patent [19]

Sekikawa et al.

[11] Patent Number: 5,133,969
[45] Date of Patent: Jul. 28, 1992

[54] ANTIMICROBIAL DISPERSION COMPOSITION

[75] Inventors: Ayako Sekikawa; Hideo Sugi; Ryoichi Takahashi; Kenji Tahara, all of Tokyo, Japan

[73] Assignee: Kurita Water Industries Ltd., Tokyo, Japan

[21] Appl. No.: 618,592

[22] Filed: Nov. 28, 1990

Related U.S. Application Data

[63] Continuation of Ser. No. 312,091, Feb. 17, 1989, abandoned.

[30] Foreign Application Priority Data

Mar. 7, 1988 [JP] Japan ................................ 63-53124
Oct. 6, 1988 [JP] Japan ................................ 63-252657

[51] Int. Cl.$^5$ ...................... A01N 25/34; A01N 25/00
[52] U.S. Cl. ...................... 424/416; 424/405; 424/78.07; 514/359; 514/439; 514/445; 514/738; 514/730; 514/739
[58] Field of Search ............ 424/416, 405, 78; 514/359, 439, 445, 738, 730

[56] References Cited

U.S. PATENT DOCUMENTS

| | | | |
|---|---|---|---|
| 4,356,115 | 10/1982 | Shibanai | 252/522 |
| 4,644,021 | 2/1987 | Toda et al. | 424/408 |
| 4,780,317 | 10/1988 | Sekikawa et al. | 424/408 |

FOREIGN PATENT DOCUMENTS

| | | |
|---|---|---|
| 54-123371 | 9/1979 | Japan . |
| 58-150577 | 9/1983 | Japan . |
| 61-53201 | 3/1986 | Japan . |
| 61-152765 | 7/1986 | Japan . |
| 62-22701 | 1/1987 | Japan . |
| 62-115072 | 5/1987 | Japan . |
| 0115072 | 5/1987 | Japan . |
| 62-142147 | 6/1987 | Japan . |
| 62-175401 | 8/1987 | Japan . |
| 62-194824 | 8/1987 | Japan . |

OTHER PUBLICATIONS

Wakabayashi et al., Chem. Abst., 108, 93, 1988, Abst. No. 152,243t.

*Primary Examiner*—F. T. Moezie
*Attorney, Agent, or Firm*—Kanesaka and Takeuchi

[57] ABSTRACT

An antimicrobial composition comprises a clathrate compound containing a water-soluble microbicide, and a dispersion medium.

For example, the composition may comprise of a clathrate compound containing a water-soluble microbicide and having a particle size of 200 mesh at maximum, said clathrate compound being formed of 5-chloro-2-methyl-4-isothiazoline-3-one and at least one polymolecular host compound selected from the group consisting of 1,1-di (2,4-dimethylphenyl)-2-propyne-1-ol; 1,1,6,6-tetra(2,4-dimethylphenyl)-2,4-hexadiyne-1,6-diol; 1,1-bis(4-hydroxyphenyl)cyclohexane; N,N,N',N'-tetra(cyclohexyl)-[1,1'biphenyl]-2,2'-dicarboxyamide; 2,2'-methylenebis(4-chlorophenol), deoxycholic acid; and 2,5-di-tert-butylhydroquinone and a dispersion medium.

5 Claims, No Drawings

ANTIMICROBIAL DISPERSION COMPOSITION

This application is a continuation of application Ser. No. 312,091, filed Feb. 17, 1989 now abandoned.

FIELD OF THE INVENTION AND RELATED ART STATEMENT

This invention relates to an antimicrobial composition. More particularly, it is a composition which can be used easily and safely as a sustained release antimicrobial agent.

The water-soluble microbicide of the isothiazoline type which is represented by formula (I) below and known as 5-chloro-2-methyl-4-isothiazoline-3-one (hereinafter referred to simply as "CMI") is widely used as a slime control agent, bactericide, algicide or fungicide in cooling water systems, water systems in the paper and pulp industry, and other water systems, including its use with an aqueous emulsion paint or adhesive or a cutting fluid, since it has a high degree of antimicrobial activity:

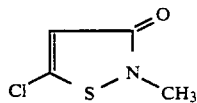
(I)

CMI is usually produced by:
(1) the halogenation of β-thioketoamide in an inert organic ester solvent, such as an acetic acid ester; or
(2) the treatment of a β-substituted thiocyanoacrylamide or thiosulfatoacrylamide with an acid to obtain isothiazolone and the halogenation thereof, as disclosed in Japanese Patent Publication No. 21240/1971.

Neither of these two methods (1) and (2) can, however, make a product which is composed solely of CMI. They can make only a mixture containing as a by-product 2-methyl-4-isothiazoline-3-one (hereinafter referred to simply as "MI") represented by formula (II) below and having an antimicrobial activity which is as low as only one-tenth of that of CMI:

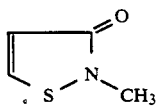
(II)

The water-soluble microbicide which is composed of CMI is produced and sol in the form of an aqueous solution which contains a large amount of metal salt as a stabilizer for CMI. When it is added to an aqueous emulsion paint or adhesive, or a cutting fluid, it is usually diluted, since the addition of an undiluted solution is likely to cause the destruction of the emulsion.

We, the applicant of this application, have found that clathrate compounds containing CMI provide sustained release microbicides which do not contain any metal salt, and yet are stable. These clathrate compounds form the subject matter of Japanese Patent Applications Laid Open Nos. 53201/1986, 22701/1987, 175401/1987 and 142147/1987.

Although a clathrate compound containing CMI is effective as a stable sustained release antimicrobial agent not containing any MI or metal salt, it is not suitable for direct use, as it is a powder. It is inconvenient to handle, and its scattering worsens the environment in which it is used.

OBJECT AND SUMMARY OF THE INVENTION

It is an object of this invention to provide an antimicrobial composition which overcomes the drawbacks of the prior art as hereinabove pointed out and enables, for example, a clathrate compound containing CMI to be used easily and in a way not causing any environmental contamination.

The antimicrobial composition of this invention comprises a clathrate compound containing a water-soluble microbicide, and a dispersion medium. CMI is a water-soluble microbicide which is particularly effective for use in the antimicrobial composition of this invention.

DETAILED DESCRIPTION OF PREFERRED EMBODIMENTS

Referring in detail to this invention, the clathrate compound containing a water-soluble microbicide is a compound formed by the molecular inclusion of a water-soluble microbicide as a guest compound in a host compound.

It is possible to use without any particular limitation any water-soluble microbicide as a guest compound if it can form a clathrate compound with an appropriate host compound. However, it is preferable to use a microbicide of the isothiazoline type, such as CMI of formula (I), or hydrazine. All of these compounds are widely used as effective water-soluble microbicides. CMI is particularly effective for the purpose of this invention.

As regards the host compound, which is a powder, it is possible to use without any particular limitation any compound that can combine with a water-soluble microbicide, such as CMI, to form a clathrate compound. Eleven polymolecular host compounds are shown below merely by way of example:

(1) 1,1,6,6-tetraphenyl-2,4-hexadiyne-1,6-diol

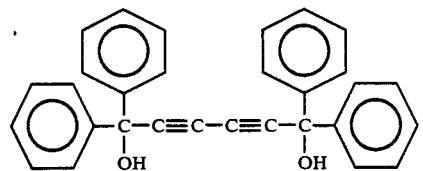

(2) 1,1-di(2,4-dimethylphenyl)-2-propyne-1-ol

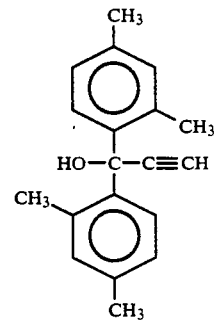

(3) 1,1,4,4-tetraphenyl-2-butyne-1,4-diol

-continued

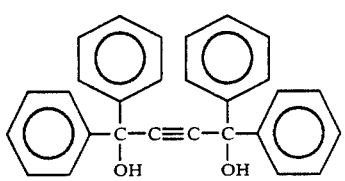

(4) 1,1'-bi-2-naphthol

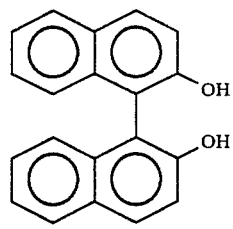

(5) 1,1,6,6-tetra(2,4-dimethylphenyl)-2,4-hexadiyne-1,6-diol

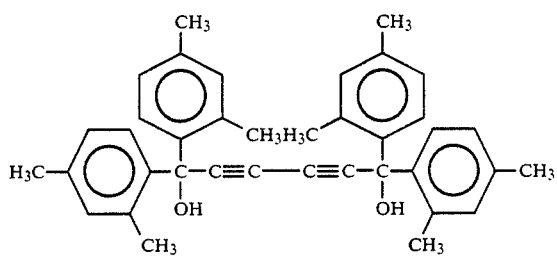

(6) 9,10-di(4-methylphenyl)-9,10-dihydroanthracene-9,10-diol

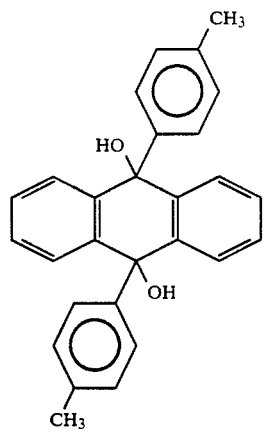

(7) 1,1-bis(4-hydroxyphenyl)-cyclohexane

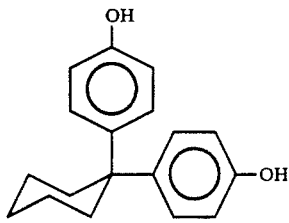

(8) N,N,N',N'-tetra(cyclohexyl)-[1,1'-biphenyl]-2,2'-dicarboxyamide

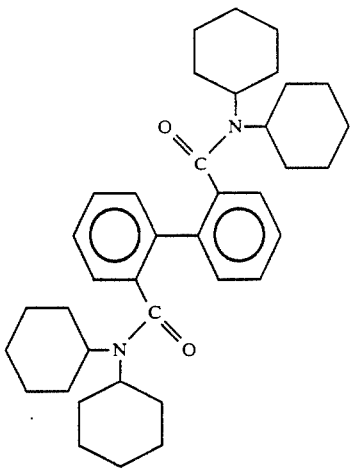

(9) 2,2'-methylenebis(4-chlorophenol)

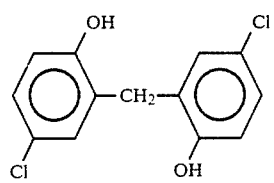

(10) deoxycholic acid

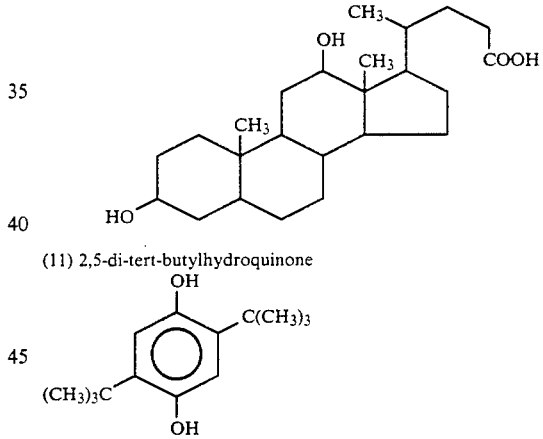

(11) 2,5-di-tert-butylhydroquinone

The clathrate compound which comprises a water-soluble microbicide and, for example, one of the host compounds listed above can be produced easily either in the presence of a solvent, or not.

When a solvent is employed, a solution or dispersion of a host compound in an ordinary water-soluble solvent such as methanol, ethanol or acetone, or in an ordinary non-water-soluble solvent or dispersant such as benzene, toluene, xylene or chloroform, is mixed with a water-soluble microbicide, such as CMI, or a mixture containing impurities, whereby a solid (or semi-solid) clathrate compound is precipitated as a reaction product. It can be collected by a customary method of filtration.

When no solvent is employed, a host compound is directly admixed in an aqueous solution of a water-soluble microbicide and the mixture is stirred. This solution need not necessarily be one containing only the microbicide, but may also contain impurities. Even if the solution may contain any byproduct or other impurities, it is possible to produce a clathrate compound in which only the desired microbicide is imprisoned, since the host compound undergoes a highly selective reaction with the microbicide.

It is possible to employ any reaction temperature in the range of 0° C. to 100° C. However, it is usually suitable to employ a temperature of, say, 10° C. to 30° C. It is sufficient to continue the reaction for a period of, say, 0.5 to 24 hours.

The clathrate compound which is produced as hereinabove described is usually a solid compound which contains 10 to 40% by weight of for example, isothiazoline microbicide, such as CMI and 60 to 90% by weight of host compound. It does not contain any metal salt that the conventional isothiazoline microbicides for use in water systems contain as a stabilizer.

The clathrate compound is dispersed in a dispersion medium to form an antimicrobial composition in the form of a suspension. The dispersion medium may be either aqueous or organic. It is preferable for the clathrate compound to have a size as small a particle size as possible, so that it may be uniformly dispersed in the dispersion medium. From a practical standpoint, it is appropriate to use a finely divided compound having a particle size not exceeding 100 mesh (Tyler).

When an aqueous dispersion medium, i.e. water, is used for dispersing, for example, a clathrate compound containing CMI as its effective microbicidal constituent, CMI is gradually dissolved in the water if the suspension has a low concentration of the clathrate compound. The effective constituent which has been dissolved in water is so unstable that it is easily decomposed and rapidly loses its microbicidal effect. The time in which the effective constituent is dissolved in water depends on the kind of host compound which the clathrate compound contains. For example, 100% of CMI is dissolved in water in about seven hours when the aqueous suspension contains 0.1% by weight of the clathrate compound which comprises the host compound shown at (7) above and CMI, or is dissolved in about 48 hours when the clathrate compound comprises the host compound shown at (9) or (10) above and CMI.

On the other hand, it has been found that if the aqueous suspension has at least a certain concentration of a clathrate compound containing CMI, CMI remains so stable that its initial concentration can be maintained even at the end of four months. When the suspension has at least a certain concentration of the clathrate compound, an equilibrium is maintained between the CMI in the clathrate compound and the CMI which has been dissolved in water, and moreover, the CMI which has been dissolved is not decomposed, but remains stable.

Therefore, it follows that the higher concentration of the clathrate compound the aqueous suspension has, the more useful it is and the higher stability of the guest compound, such as CMI, it can maintain. From a practical standpoint, however, it is appropriate to prepare an aqueous suspension containing, say, 10 to 50% by weight of the clathrate compound.

If the aqueous dispersion medium is so low in viscosity that the clathrate compound undergoes sedimentation when it is left at a standstill, it is possible to obtain a stable suspension if a high molecular substance or surface active agent which is compatible with the dispersion medium is added in an appropriate quantity as a sedimentation inhibitor. If a high molecular substance is added, it is possible to use, for example, methyl cellulose, ethyl cellulose, hydroxyethyl cellulose, hydroxypropyl starch, polyvinyl alcohol, polyvinyl pyrrolidone, polyvinyl methyl ether, polyacrylamide, xanthane gum, guar gum, or carboxymethyl cellulose. In case of a synthetic high molecular substance, its molecular weight is within the range of from 1,000 to 5,000,000. If a surface active agent is employed, it is possible to use, for example, the condensation product of sodium naphthalenesulfonate and formalin, or of sodium melaminesulfonate and formalin, sodium lauryl sulfate, sodium lauryl benzenesulfonate, or polyoxyethylene alkyl ether.

When an organic dispersion medium is employed, it is possible to use without any particular limitation any substance that can maintain the particles of the clathrate compound in a stable state of suspension and allows the microbicide to remain stable without being decomposed and retain its antimicrobial activity, even if it may be dissolved in the dispersion medium. The following is a list of examples of the organic dispersion mediums which can be employed:

(a) Alcohols, such as ethylene glycol, propylene glycol, glycerin and polyglycerin;
(b) Liquid paraffin;
(c) Xylene or toluene;
(d) Vegetable oils, such as castor oil, soybean oil, olive oil and rapeseed oil;
(e) Terpenes, such as hinoki oil; and
(f) Surface active agents, such as polyoxyethylene alkyl ether.

It is possible to use either one of these or other substances or a mixture of two or more substances.

The higher the concentration of the clathrate compound, the greater advantages the suspension has, as has already been mentioned with respect to the aqueous suspension. From a practical standpoint, however, it is suitable to prepare a suspension containing, say, 10 to 50% by weight of the clathrate compound.

If the organic dispersion medium which is employed is so low in viscosity that the clathrate compound undergoes sedimentation when the suspension is left at a standstill, it is possible to obtain a stable suspension if a high molecular substance or dispersing agent which is compatible with the dispersion medium is added in an appropriate quantity as a sedimentation inhibitor. If a high molecular substance is added, it is possible to use, for example, a copolymer of alkyl methacrylate and diethylaminoethyl methacrylate, of alkyl methacrylate and N-vinyl-2-pyrrolidone acrylate, of alkyl methacrylate and polyethylene glycol methacrylate, of dodecyl fumarate and diethylaminoethyl methacrylate, or of styrene and maleic acid which has a molecular weight within the range of from 1,000 to 5,000,000. If a dispersing agent is employed, it is possible to use, for example, a succinimide, succinic acid ester, polyalkyl glycol carbonate, polyalkylene glycol carbamic acid ester, alkylbenzenesulfonic acid, or nonionic surface active agent.

The antimicrobial composition of this invention may further contain various kinds of modifiers and additives.

The water-soluble microbicide has a solid state in the clathrate compound and is gradually dissolved therefrom. The microbicide in the clathrate compound is so stable as not to require the use of any metal salt, etc. as a stabilizer. Moreover, the clathrate compound makes the microbicide less toxic and less irritant to the skin, and prevents it from reacting with any other substance and losing its antimicrobial activity. Therefore, the clathrate compound according to this invention is effective as a sustained release antimicrobial agent which can maintain its antimicrobial activity for a very long period of time.

The antimicrobial composition of this invention, which comprises the clathrate compound dispersed in an aqueous or organic dispersion medium, is a stable suspension which retains the high antimicrobial activity of the clathrate compound, and is, therefore, very easy to handle or use. It causes no scattering of any fine powder, but can maintain in a good condition the environment in which it is used. Moreover, it can be used effectively in a wide variety of water systems without destroying any aqueous emulsion, as it does not contain any metal salt as a stabilizer.

The antimicrobial composition of this invention retains the advantages which the water-soluble microbicide possesses in the clathrate compound, i.e.:

(1) The microbicide is dissolved in water so slowly that its antimicrobial activity can be maintained for a long time;

(2) The clathrate compound makes the microbicide less toxic and less irritant to the skin, and thereby improves the safety of the environment in which it is used; and (3) The clathrate compound prevents the microbicide from reacting with any other substance and losing its antimicrobial activity.

The antimicrobial composition of this invention is particularly effective when it contains CMI as the water-soluble microbicide.

The invention will now be described more specifically with reference to a variety of examples. It is, however, to be understood that the following description is not intended to limit the scope of this invention, but that variations or modifications may be easily made by anybody of ordinary skill in the art without departing from the scope of this invention which is defined by the appended claims.

EXAMPLE 1

Tests on the Dispersion Stability of Clathrate Compounds in an Aqueous Dispersion Medium and Their Antimicrobial Activity A powdery clathrate compound having a particle size not exceeding 22 mesh was prepared by reacting 1,1-bis-(4-hydroxyphenyl)cyclohexane, 2,2'-methylenebis(4-chlorophenol) or deoxycholic acid with an isothiazoline microbicide comprising a mixed solution of CMI and MI (an aqueous solution of the Rohm & Haas product known as KATHON 886). Each clathrate compound was dispersed in an aqueous dispersion medium (water) to form a suspension, and it was examined for stability and antimicrobial activity. The results are shown in Table 1 below. Each suspension contained 30% by weight of the clathrate compound.

Referring first to the examination of each suspension for stability, it was left to stand at room temperature for three months and its appearance was inspected with respect to two aspects, i.e. fluidity and phase separation. The symbols used in Table 1 to indicate the results have the following meanings, respectively:

Fluidity

○: Good;
Δ: Poor;
x: Bad.

Phase separation

○: No phase separation occurred;
x: The separation of solid and liquid phases occurred.

After the three months, each suspension was also examined for its antimicrobial activity employing E. Coli. Its antimicrobial activity was determined after 24 hours of its exposure to E. Coli and compared with that of a solution of KATHON 886 having the same concentration. The symbols used to indicate the results were:

○: The antimicrobial activity of the suspension was at least equal to that of the KATHON 886 solution;
Δ: The former was somewhat inferior to the latter.

TABLE 1

| No. | Host Compound | Stability Fluidity | Phase separation | Antimicrobial activity |
|---|---|---|---|---|
| 1 | 1,1-bis-(4-hydroxyphenyl)cyclohexane | x | ○ | ○ |
| 2 | 2,2'-methylenebis-(4-chlorophenol) | Δ | ○ | ○ |
| 3 | Deoxycholic acid | ○ | x | ○ |

As is obvious from Table 1, Suspension No. 2 was relatively good in both of dispersion stability and antimicrobial activity, while the other two suspensions were inferior in dispersion stability.

EXAMPLE 2

Improvement in Dispersion Stability

Example 1 was repeated for preparing suspensions and examining each of them for dispersion stability after three months, except that each clathrate compound had been crushed into a finer powder having a particle size of 200 mesh to achieve an improved dispersion stability. The suspension corresponding to No. 3 in Table 1 was found to be of improved dispersion stability, as it did not show any phase separation.

EXAMPLE 3

Improvement in Dispersion Stability

Example 1 was repeated for preparing suspensions corresponding to Nos. 1 and 2 in Table 1 and examining each of them for dispersion stability after three months, except that 0.025% by weight of xathantane gum and 0.1% by weight of polyvinyl pyrrolidone had been added to each suspension to improve its dispersion stability. Both of the suspensions were found to be of improved dispersion stability, as they showed good fluidity.

EXAMPLE 4

Mixing of Suspensions with an Aqueous SBR Emulsion

One part by weight of each of the compositions of this invention shown at Nos. 1 to 3 in Table 1 was mixed with one part by weight of an aqueous emulsion of SBR under stirring. Each mixture was examined for uniformity. All of the compositions could be mixed with the emulsion uniformly without destroying it.

When one part by weight of KATHON 886 was mixed with one part by weight of an aqueous emulsion of SBR, however, the emulsion was destroyed and produced a sediment.

EXAMPLE 5

Tests for Dissolution in Water

One gram of each of the compositions shown at Nos. 1 to 3 in Table 1 was placed in one liter of water. The water was stirred at a speed of 488 rpm at a temperature of 25° C. and the amounts of the effective constituent (CMI) which had been dissolved in the water were measured from time to time as shown in Table 2. The results are shown in Table 2.

The dissolution of KATHON 886 was likewise examined for the sake of comparison. The results are shown in Table 2.

The results shown in Table 2 confirm the sustained release of the effective constituent from the antimicrobial compositions according to this invention.

TABLE 2

| Composition No. | Dissolution of effective constituent (wt. %) | | | | | | |
|---|---|---|---|---|---|---|---|
| | 15 min. | 30 min. | 1 h. | 2 h. | 4 h. | 10 h. | 24 h. |
| 1 | 80 | 85 | 92 | 95 | 100 | — | — |
| 2 | 35 | 44 | 54 | 63 | 73 | 89 | 100 |
| 3 | 17 | 20 | 26 | 37 | 48 | 84 | 100 |
| KATHON 886 | 100 | — | — | — | — | — | — |

EXAMPLE 6

Dispersion Stability of Clathrate Compounds in Organic Dispersion Mediums and Their Antimicrobial Activity Example 1 was repeated for preparing suspensions and evaluating each of them for dispersion stability and antimicrobial activity, except that various organic dispersion mediums were employed as shown in Table 3, and that the antimicrobial activity of each composition was determined after one month of its exposure to *E. Coli*. The results are shown in Table 3.

As is obvious from Table 3, Suspensions Nos. 4 to 7 were good in both of stability and antimicrobial activity, and were found to be capable of immediate use, while the other suspensions were inferior in stability or antimicrobial activity.

TABLE 3

| No. | Dispersion medium | Stability | | Antimicrobial activity |
|---|---|---|---|---|
| | | Fluidity | Phase separation | |
| 4 | Glycerin | o | o | o |
| 5 | Liquid paraffin | o | o | o |
| 6 | Silicone oil | o | o | o |
| 7 | Xylene | o | o | o |
| 8 | Ethylene glycol | o | x | Δ |
| 9 | Propylene glycol | o | x | o |
| 10 | Polyoxyethylene alkyl ether | o | x | o |
| 11 | Polyglycerin | x | o | o |
| 12 | Hinoki oil | o | x | o |
| 13 | Castor oil | o | o | Δ |
| 14 | Soybean oil | o | x | o |
| 15 | Olive oil | o | x | o |
| 16 | Rapeseed oil | o | x | Δ |

EXAMPLE 7

Improvement in Dispersion Stability

Example 6 was repeated for preparing suspensions corresponding to Nos. 4 to 16 in Table 3 and evaluating each of them for stability after one month, except that the clathrate compound had been crushed into a finer powder having a particle size of 200 mesh. Suspensions Nos. 8 to 10, 12 and 14 to 16 were all improved in stability, as no phase separation was found in any of the corresponding suspensions.

EXAMPLE 8

Mixing of Compositions with an Aqueous SBR Emulsion

One part by weight of each of the antimicrobial compositions of this invention shown at Nos. 4 to 7 in Table 3 was mixed with one part by weight of an aqueous emulsion of SBR under stirring. Each mixture was examined for uniformity. All of the compositions could be mixed with the emulsion uniformly without destroying it.

When one part by weight of KATHON 886 was mixed with one part by weight of an aqueous emulsion of SBR, however, the emulsion was destroyed and produced a sediment, as has already been stated in Example 4.

EXAMPLE 9

Tests for Dissolution in Water

One gram of each of the compositions shown at Nos. 4 and 5 in Table 3 was placed in one liter of water. The water was stirred at a speed of 488 rpm at a temperature of 25° C. and the amounts of the effective constituent (CMI) which had been dissolved in water were measured from time to time. The results are shown in Table 4.

A similar test was conducted on KATHON 886 for the sake of comparison. The results are shown in Table 4.

TABLE 4

| Composition No. | Dissolution of effective constituent (wt. %) | | | | | |
|---|---|---|---|---|---|---|
| | Time elapsed | | | | | |
| | 10 min. | 30 min. | 1 h. | 2 h. | 3 h. | 5 h. |
| 4 | 88 | 95 | 97 | 97 | 99 | 100 |
| 5 | 39 | 68 | 89 | 94 | 94 | 96 |
| KATHON 886 | 100 | — | — | — | — | — |

The results shown in Table 4 confirm the sustained release of the effective constituent from the antimicrobial compositions of this invention.

What is claimed is:

1. An antimicrobial dispersion composition comprising:

a clathrate compound containing a water-soluble microbicide and having a particle size of 200 mesh at maximum, said clathrate compound being formed of 5-chloro-2-methyl-4-isothiazoline-3-one and at least one polymolecular host compound selected from the group consisting of 1,1,6,6-tetra(2,4-dimethylphenyl)-2,4-hexadiyne-1,6-diol; 1,1-bis(4-hydroxyphenyl)cyclohexane; N,N,N',N'-tetra(cyclohexyl)-[1,1'-biphenyl]-2,2'-dicarboxyamide; 2,2'-methylenebis(4-chlorophenol), deoxycholic acid; and 2,5-di-tert-butylhydroquinone; and water for retaining the clathrate compound with a particle size of 200 mesh at maximum to be equally dispersed therein, said clathrate compound being retained in the water at 10–50 wt. % so that the clathrate compound is stably retained in the water without decomposition of the microbicide.

2. An antimicrobial composition as set forth in claim 1, wherein said clathrate compound comprises 10 to 40% by weight of said microbicide and 60 to 90% by weight of said host compound.

3. An antimicrobial composition as set forth in claim 1, further containing a sedimentation inhibitor of high molecular weight or a surface active agent.

4. An antimicrobial dispersion composition comprising:
a clathrate compound containing a water-soluble microbicide and having a particle size of 200 mesh at maximum, said clathrate compound being formed of 5-chloro-2-methyl-4-isothiazoline-3-one and at least one polymolecular host compound selected from the group consisting of 1,1,6,6-tetra(2,4-dimethylphenyl)-2,4-hexadiyne-1,6-diol; 1,1-bis(4-hydroxyphenyl)cyclohexane; N,N,N',N'-tetra(cyclohexyl)-[1,1'-biphenyl]-2,2'-dicarboxyamide; 2,2'-methylenebis(4-chlorophenol), deoxycholic acid; and 2,5-di-tert-butylhydroquinone; and
an organic dispersion medium for retaining the clathrate compound with a particle size of 200 mesh at maximum to be equally dispersed therein, said clathrate compound being retained in the dispersion medium at 10-15 wt. % so that the clathrate compound is stably retained in the dispersion medium without decomposition of the microbicide, said organic dispersion medium being at least one member selected from the group consisting of alcohols, liquid paraffin, xylene, vegetable oils, terpenes, and surface active agents.

5. An antimicrobial composition as set forth in claim 4, further containing a sedimentation inhibitor of high molecular weight or a dispersing agent.

* * * * *